(12) United States Patent
Volker et al.

(10) Patent No.: US 9,026,376 B2
(45) Date of Patent: May 5, 2015

(54) CORROSION MONITORING

(75) Inventors: Arno Willem Frederik Volker, Delft (NL); Joost Gerardus Petrus Bloom, Delft (NL); Arjan Mast, Rotterdam (NL); Pieter Jacobus Gijsbertus van Beek, Den Haag (NL)

(73) Assignee: Nederlandse Organisatie voor toegepast-natuurwetenschappelijk onderzoek TNO (NL)

( * ) Notice: Subject to any disclaimer, the term of this patent is extended or adjusted under 35 U.S.C. 154(b) by 759 days.

(21) Appl. No.: 13/055,449

(22) PCT Filed: Jul. 22, 2009

(86) PCT No.: PCT/NL2009/050452
§ 371 (c)(1),
(2), (4) Date: Apr. 21, 2011

(87) PCT Pub. No.: WO2010/011140
PCT Pub. Date: Jan. 28, 2010

(65) Prior Publication Data
US 2011/0191035 A1    Aug. 4, 2011

(30) Foreign Application Priority Data

Jul. 22, 2008   (EP) .................................. 08160912
Apr. 8, 2009    (EP) .................................. 09157642

(51) Int. Cl.
*G01N 29/04*   (2006.01)
*G01N 29/07*   (2006.01)
(Continued)

(52) U.S. Cl.
CPC .............. *G01N 29/041* (2013.01); *G01N 29/07* (2013.01); *G01N 29/348* (2013.01);
(Continued)

(58) Field of Classification Search
USPC ............................................. 702/39
See application file for complete search history.

(56) References Cited

U.S. PATENT DOCUMENTS

| 5,965,818 A * | 10/1999 | Wang ............................... 73/598 |
| 6,294,912 B1 | 9/2001 | Kwun |
| 6,934,406 B1 | 8/2005 | Nakano |

FOREIGN PATENT DOCUMENTS

| CN | 101093170 A | 12/2007 |
| GB | 2 403 009 A | 12/2004 |

(Continued)

OTHER PUBLICATIONS

Graham R Edwards, Detection of corrosion in offshore risers using guided ultrasonic waves, Paper presented at 26th International Conference on Offshore Mechanics and Arctic Engineering, OMAE 2007, San Diego, California, Jun. 10-15, 2007. Paper No. 29407., p. 1-8.*

(Continued)

*Primary Examiner* — Tung S Lau
(74) *Attorney, Agent, or Firm* — Kilpatrick Townsend & Stockton LLP

(57) ABSTRACT

A method of modelling a surface of an object by using ultrasonic waves transmitted along the surface comprises the steps of:
  transmitting the ultrasonic waves along paths along the surface, and
  determining travel times of the ultrasonic waves along the paths.
At least some of the ultrasonic waves exhibit an S0 mode and have a frequency-dependent velocity. This velocity (c) is relatively high for frequencies up to a first bending point (BP1), decreasing relatively rapidly for frequencies between the first bending point (BP1) and a second bending point (BP2), and relatively low for frequencies beyond the second bending point (BP2). The ultrasonic waves have a frequency range which lies at or below the first bending point (BP1).

15 Claims, 4 Drawing Sheets

(51) Int. Cl.
*G01N 29/34* (2006.01)
*G01N 29/44* (2006.01)

(52) U.S. Cl.
CPC ..... *G01N 29/4472* (2013.01); *G01N 2291/011* (2013.01); *G01N 2291/0423* (2013.01); *G01N 2291/2634* (2013.01)

(56) References Cited

FOREIGN PATENT DOCUMENTS

| | | |
|---|---|---|
| JP | 2007-3537 A | 1/2007 |
| JP | 2007-232373 A | 9/2007 |
| RU | 2156455 C1 | 9/2000 |
| WO | 2005010522 A2 | 2/2005 |
| WO | 2007068979 A1 | 6/2007 |

OTHER PUBLICATIONS

Japanese Office Action mailed Jul. 23, 2013 in Application No. JP2011-520007.
Chinese Office Action mailed Nov. 20, 2012 in Application No. CN 200980129013.6.
Search Report dated Jan. 25, 2013 in Application No. RU2011106497/28 (009241).
International Search Report and Written Opinion mailed Jan. 27, 2010 in PCT Application No. PCT/NL2009/050452.

\* cited by examiner

CORROSION MONITORING

CROSS-REFERENCES TO RELATED APPLICATIONS

This application is a National Stage of International Application No. PCT/NL2009/050452, filed Jul. 22, 2009, and which claims the benefit of European Patent Applications Nos. 08160912.5, filed Jul. 22, 2008 and 09157642.1, filed Apr. 8, 2009 the disclosures of which are incorporated herein by reference.

The present invention relates to corrosion monitoring. More in particular, the present invention relates to corrosion monitoring using single path or multipath ultrasound measurements to examine the condition of an object, such as a metal pipe, and to optionally create a representation of the object using tomographic methods.

A method and device for corrosion monitoring using tomography are described in European Patent Application 07102653 (TNO), published on 20 Aug. 2008 as EP 1 959 229 A1 and on 28 Aug. 2008 as WO 2008/103036 A1.

In said European Patent Application, ultrasonic signals are sent along the surface of an object from a transmitting unit to a receiving unit, and only the direct signals are analysed. Direct signals are the signals which reach a receiving unit without travelling around the circumference of the (cylindrical or spherical) object, at least for less than 360°. However, it is also possible to use multipath or indirect signals, that is signals travelling around the circumference of the object for more than 360°. This leads to the phenomenon that a receiving unit will receive multiple signals, some of which have travelled around the object at an acute angle to the length of the (cylindrical) object. This angle allows certain deteriorations to be examined in more detail, as not only the width (in the circumferential direction) but also the length (in the longitudinal direction) of the deterioration can be estimated.

Figure 3:
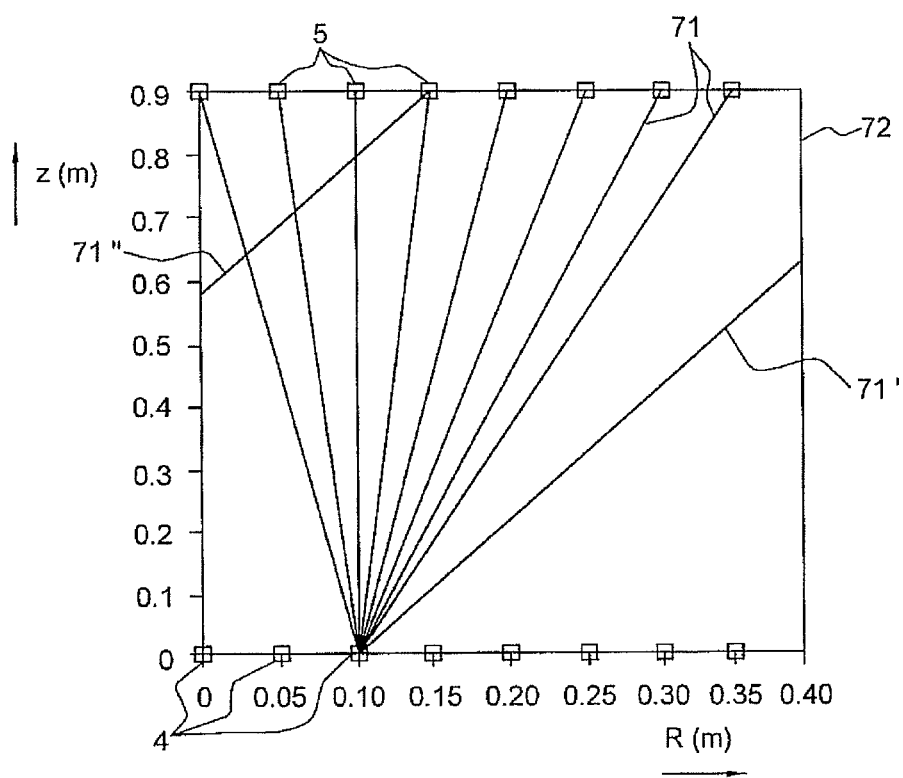
Figure 7:
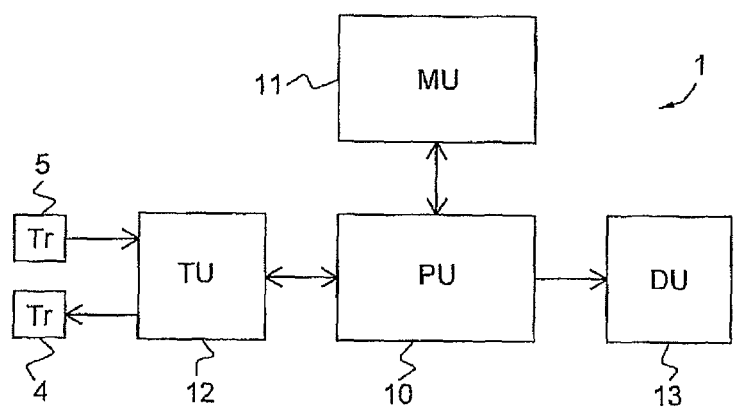

Japanese Patent Application JP 2007-3537 (Hitachi) discloses a method of monitoring pipes using both direct and indirect sound waves. FIG. 7 of said Japanese Patent Application shows how waves travelling at different angles can be utilized. FIG. 3 of the same patent application shows a diagram of the relative speed (vertical axis) versus the product of thickness and frequency, for different modes of the waves (Lamb waves, in the particular example): A0 and S0. It can be seen, as is well known, that the curve representing the S0 mode exhibits two bending points (or "points of inflection"): a first one at a relatively low frequency (in the example referred to, the product of thickness and frequency is approximately equal to 2) and a second one at a relatively high frequency (in the example referred to, the product of thickness and frequency is approximately equal to 3). As a non-dispersive wave is used, this must be the SH0 mode which has a uniform velocity (FIG. 10). However, dispersion correction is also used, which means that the velocity of the S0 mode is equal to the velocity of the SH0 mode.

It can therefore be concluded from said Japanese Patent Application that the proposed working range is at or around the second bending point, and is given by the intersection of the curve of the S0 mode (FIG. 3) and the (substantially horizontal) line representing the SH0 mode (FIG. 10). This is confirmed by the fact that the Japanese Patent Application mentions a frequency of 500 kHz (=0.5 MHz) and a thickness of 6 mm, which results in a frequency times thickness value of 3 MHz·mm, and which corresponds exactly with the second bending point.

It can be shown, however, that in some applications the frequencies at the second bending point experience an extremely high attenuation, thus making the Prior Art monitoring method practically useless in those applications. This is in particular the case when liquid-filled pipes or vessels are monitored, as the liquid resists compression and thus causes a very high attenuation.

It is an object of the present invention to overcome these and other problems of the Prior Art and to provide a method and system for ultrasonic monitoring and/or modelling which does not have a high attenuation in its working range, even when used for liquid-filled pipes or vessels.

Accordingly, the present invention provides a method of modelling a surface of an object by using ultrasonic waves transmitted along the surface, the method comprising the steps of:
  transmitting the ultrasonic waves along paths along the surface, and
  determining travel times of the ultrasonic waves along the paths,
wherein at least some of the ultrasonic waves exhibit an S0 mode and have a frequency-dependent velocity, which velocity is relatively high for frequencies up to a first bending point, decreasing relatively rapidly for frequencies between the first bending point and a second bending point, and relatively low for frequencies beyond the second bending point, which method is characterised in that the ultrasonic waves have a frequency range which lies at or below the first bending point.

By using a frequency range at or below the first bending point, a significantly lower attenuation is achieved while otherwise retaining the advantage of the Prior Art method. Accordingly, the extremely high attenuation of the Prior Art is avoided and the method can be used for liquid-filled objects, such as pipes and vessels. In addition, by using an operating range at or below the first bending point, the steep part of the curve between the bending points is used to achieve the highest sensitivity to variations in the wall thickness of the object (typically, but not exclusively, a pipe or vessel).

It is noted that the frequency range mentioned above may have a relatively narrow bandwidth and may therefore be referred to as a frequency, rather than a frequency band. In practice, a frequency range comprising multiple frequencies will typically be used. A preferred bandwidth of the frequency range is less than 150 kHz, more preferably less than 120 kHz, although frequency ranges having a bandwidth of less than 100 kHz, for example 50 kHz, may also be used.

Although the frequency (range) used according to the present invention will depend on the wall thickness of the pipe or vessel, the product of frequency and thickness is preferably less than approximately 2 MHz·mm (or kHz·m), which at a wall thickness of 6 mm amounts to a frequency range of less than approximately 0.33 MHz. Accordingly, the frequency range is chosen such that the product of wall thickness and frequency in said frequency range is equal to or less than 2.0 MHz·mm.

The ultrasonic waves preferably comprise pulsed waves. It is further preferred that the ultrasonic waves comprise guided waves and/or Rayleigh waves.

The method of the present invention is particularly advantageous when some signal paths extend at least once around the circumference of the object, resulting in multiple arrivals of ultrasonic waves at certain transducer units.

The ultrasonic signals can be used for monitoring and/or for modelling, for example modelling using tomographic methods.

The present invention additionally provides a computer program product for carrying out the method defined above. A computer program product may comprise a set of computer executable instructions stored on a data carrier, such as a CD or a DVD. The set of computer executable instructions, which allow a programmable computer to carry out the method as defined above, may also be available for downloading from a remote server, for example via the Internet.

The present invention also provides a device which operates at or below the first bending point of the S0 curve. More in particular, the present invention provides a device for modelling a surface of an object by using ultrasonic waves transmitted along the surface, the device comprising:
- a first transducer and at least one second transducer, the first transducer and each second transducer defining paths along the surface,
- a transmission unit for transmitting the ultrasonic waves along the paths from the first transducer to each second transducer, and
- a processing unit arranged for determining travel times of the ultrasonic waves along the paths, wherein at least some of the ultrasonic waves exhibit an S0 mode and have a frequency-dependent velocity, which velocity is relatively high for frequencies up to a first bending point, decreasing relatively rapidly for frequencies between the first bending point and a second bending point, and relatively low for frequencies beyond the second bending point, which device is characterised in that the ultrasonic waves have a frequency range which lies at or below the first bending point.

The present invention further provides a system for monitoring objects, the system comprising a device as defined above, wherein the object preferably is a pipeline, more preferably a pipeline for transporting liquids.

Figure 1:
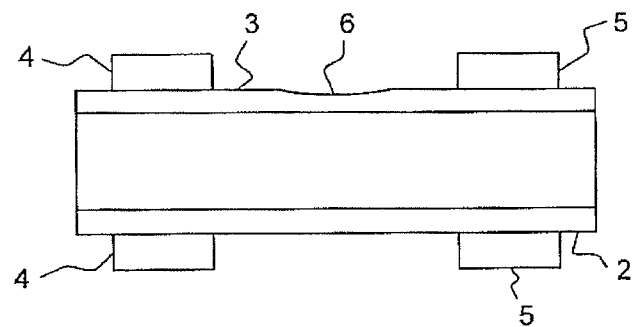

The present invention will further be explained below with reference to exemplary embodiments illustrated in the accompanying drawings, in which:

FIG. 1 schematically shows an object of which a surface is modelled in accordance with the present invention.

Figure 2:
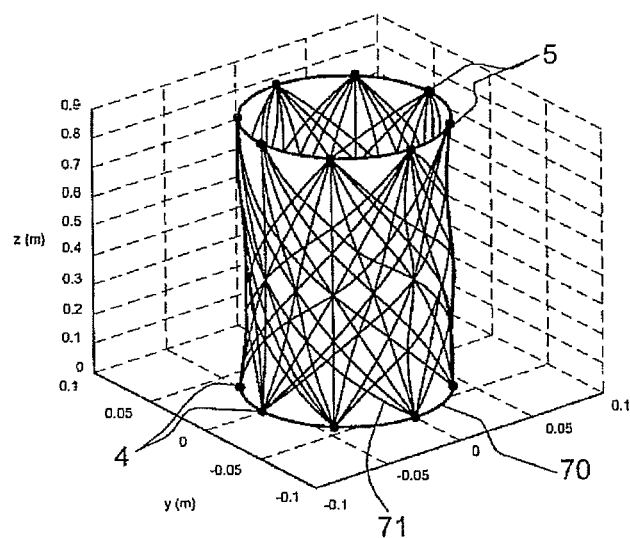

FIG. 2 schematically shows a 3-dimensional object model which may be produced in accordance with the present invention.

FIG. 3 schematically shows a 2-dimensional object model which may be produced in accordance with the present invention.

Figure 4:
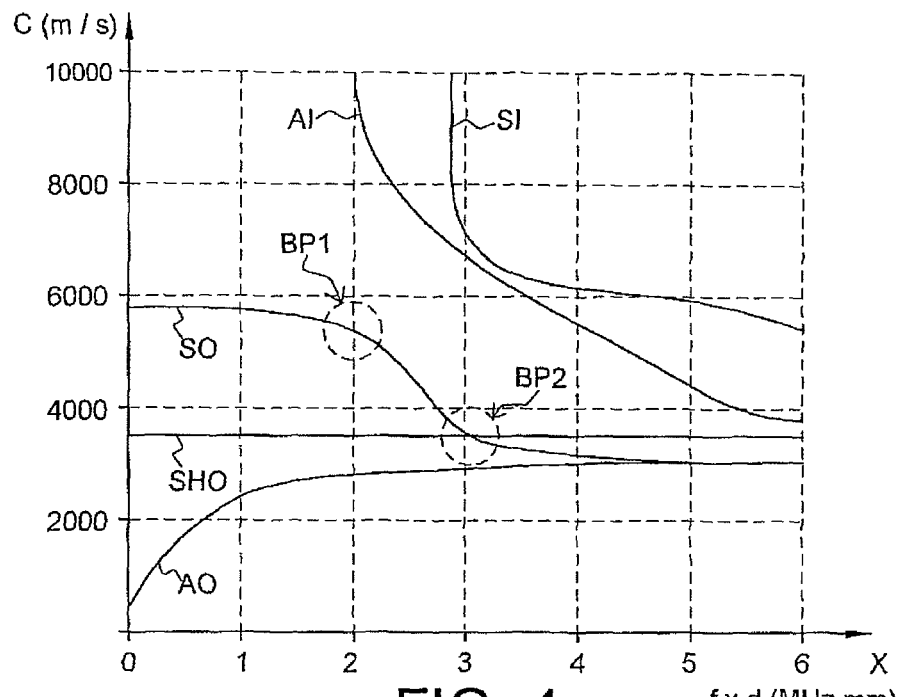

FIG. 4 schematically shows the relationships between the velocity of the ultrasonic waves and the product of frequency and wall thickness for several modes of the ultrasonic waves, as used in the present invention.

Figure 5:
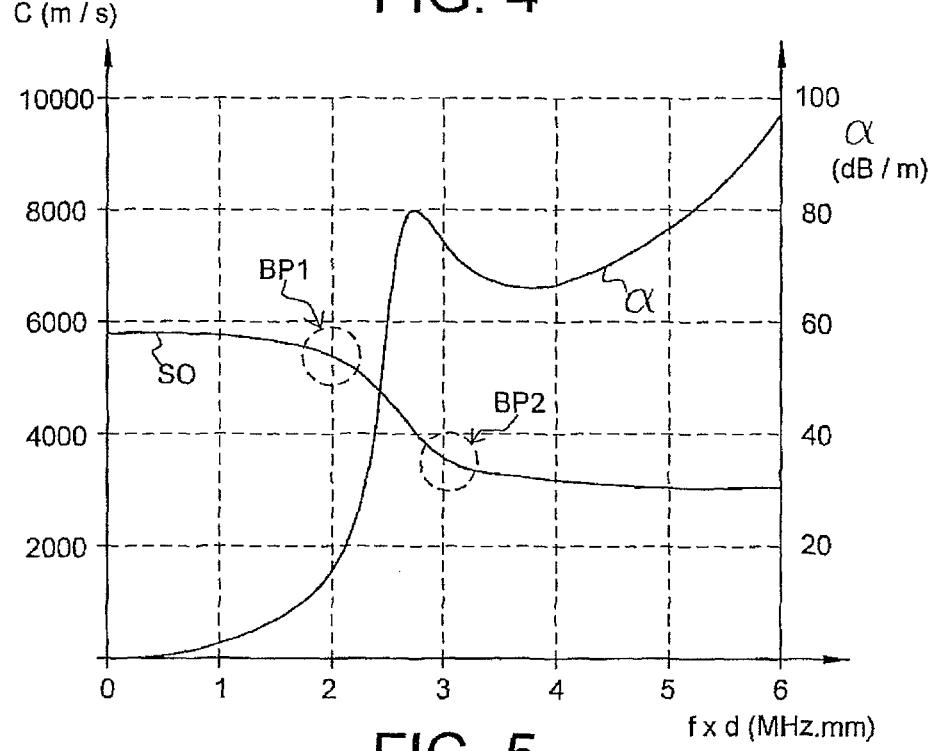

FIG. 5 schematically shows the S0 mode relationship of FIG. 4 together with the attenuation as a function of the product of frequency and wall thickness.

Figure 6A:
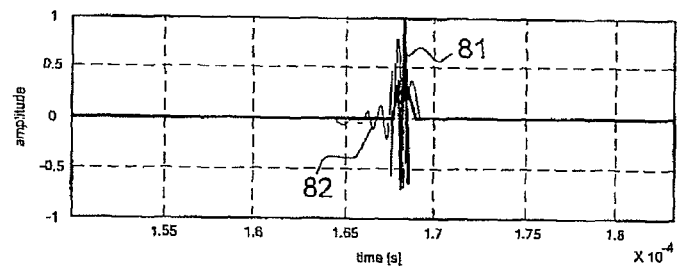
Figure 6B:
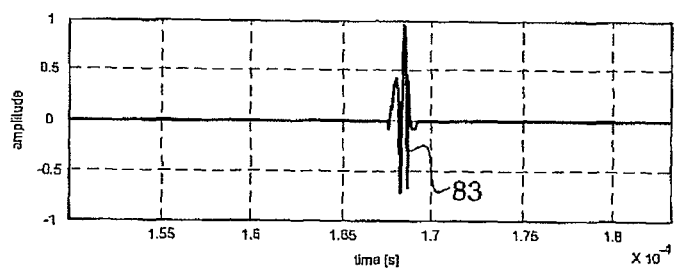

FIGS. 6A & 6B schematically show ultrasonic pulses used in the present invention.

FIG. 7 schematically shows a surface modelling device according to the present invention.

The pipe 2 shown merely by way of non-limiting example in FIG. 1 comprises a surface 3 which is to be modelled. In the example shown, the surface 3 has a recessed section 6 which may be caused by corrosion, for example. By suitably modelling the surface 3, the extent and (relative) height of the recessed section 6 may be determined.

First transducer units 4 and second transducer units 5 are mounted on the pipe 2, on either side of the surface 3. Although both the first and the second transducer units may be capable of transmitting and receiving ultrasonic waves, in the present invention the first transducer units 4 are used for transmitting ultrasonic pulsed waves while the second transducer units 5 are used for receiving these waves. The transducer units may be known per se and may be piezo-electric units.

The pulsed waves or pulses produced by the first transducers 4 have a defined duration of, for example, several µs (microseconds). The actual duration may depend on the particular application, for example the dimensions and mutual distances of the transducer units. The number of transducers may vary. At least one first transducer 4 and at least one second transducer 5 should be provided, although it is preferred to use multiple second transducers 5, for example two, three, four, eight of more second transducers 5. Using a plurality of second transducers 5 results in a plurality of paths travelled by the pulsed waves and hence an improved modelling of the surface. Similarly, it is preferred to use more than one first transducer 4. In the example of FIGS. 2 and 3, eight first transducers 4 and eight second transducers 5 are used, although the invention is not limited to these particular numbers. The transducers of a plurality of first and/or second transducers are preferably evenly spaced, although this is not essential.

An exemplary three-dimensional model is illustrated in FIG. 2, while the paths travelled by the pulsed waves are illustrated by way of a two-dimensional model in FIG. 3. The three-dimensional model 70 of FIG. 2 is based upon the two-dimensional model 72 of FIG. 3.

The model 70 of FIG. 2 represents the (outer) surface of a pipe, for example the pipe 2 of FIG. 1. The x-axis and y-axis extend in a cross-sectional plane of the tubular model, while the z-axis extends in its longitudinal direction. The dimensions of this example are provided in meters (m). The three-dimensional model of FIG. 2 is in fact a reconstruction of the object 2 of FIG. 1. Three-dimensional reconstructions are known per se in the field of tomography.

The surface modelled in FIG. 2 extends between a set of first transducers 4 and a set of second transducers 5. Paths 71 extend between each of the first transducer 4 and each of the second transducers 5. The travel times of the pulses along these paths are proportional to the lengths of the paths. A path which extends along a smooth, straight surface will be shorter than a path crossing the recess 6 of FIG. 1. Accordingly, the travel times along these paths will differ and the pulses will arrive at different times.

The model will calculate the arrival times of the pulses along the various paths. If the model initially assumes all paths to have equal lengths, a discrepancy between the measured travel times and the calculated travel times will occur for the paths crossing the recess 6. This discrepancy can be compensated by adjusting the model. Initial values of the model may be based upon measurements of the actual object (such as a pipe) and/or upon theoretical considerations.

In the two-dimensional example of FIG. 3, the horizontal axis extends along the circumference R of the tubular model, while the z-axis extends in its longitudinal direction. The dimensions are provided in meters (m).

As can be seen in FIG. 3, first transducers 4 and second transducers 5 are evenly spaced along the circumference of the model. Pulses produced by the first transducers will be detected by the second transducers. The arrival times, and hence the travel times, will correspond at least approximately to the set of paths 71 extending between each first transducer 4 and the second transducers 5. For the sake of clarity of the drawing, only one such set of paths 71 is shown in FIG. 3.

As explained above, the model contains information about the surface (3 in FIG. 1) of the object. This information may comprise a set of values representing the (relative or absolute) height of the surface in a number of points. As illustrated in FIG. 1, the surface height at the recess 6 is smaller than at the first transducer 4. In order to accurately model the surface, a large number of surface points are required, for example hundreds or even thousands of surface points.

The measured travel times are determined by subtracting transmission times of pulses from their arrival times. The transmission times are typically determined by recording the points in time at which an activation signal is sent to a first transducer unit, while the arrival times are typically determined by recording the points in time at which detection signals are received from the second transducer units.

Then the calculated travel times are compared with the measured travel times and any discrepancies are recorded. An optimisation procedure, which may be known per se, is then used to optimise the model such that the discrepancies are removed. Suitable known optimisation procedures are the Levenberg-Marquardt and the Gauss-Newton procedures.

In the method of the present invention, surface waves are preferably used. Surface waves have the advantage that each pulse obtains information of a path, not just a point. It has been found that Rayleigh waves are very suitable surface waves as they follow the surface. As a result, their travel times provide very accurate information on the surface structure.

However, guided waves are also very suitable, in particular when not only information concerning the surface but also concerning the wall thickness of the object is required. In particular, the advantageous dispersive behaviour of guided waves is utilized: given the frequency, the propagation velocity of the waves depends on the wall thickness. Accordingly, any measured velocity changes are indicative of wall thickness variations. A combination of Rayleigh (pulsed) waves and surface (pulsed) waves may also be used.

It is further shown in FIG. 3 that some ultrasonic wave paths 71 extend from a transducer unit 4 directly to a transducer unit 5, thus taking the shortest route between the transducer units. Other paths travel around the circumference of the object, sometimes over more than 360°, before reaching a transducer unit 5. In FIG. 3, this is illustrated by the path 71' which continues as path 71" and extends over more than 360° around the circumference of the object (it is noted that the two-dimensional surface model 72 of FIG. 3 is a representation of the three-dimensional surface model 70 of FIG. 2, which represents a substantially cylindrical surface). It can be seen that the (indirect) path 71" reaches the same transducer unit 5 as a (direct) path 71: the transducer 5 receives ultrasonic waves from multiple paths.

The velocity of the ultrasonic waves travelling over the surface of the object depends on various factors, including the frequency of the waves, the thickness of the object (when the surface is the surface of a wall of the object, the velocity depends on the wall thickness), and the particular mode of the waves, such as symmetrical (S) modes and asymmetrical (A) modes. In FIG. 4 the velocity c is represented (in m/s) as a function of the product (in MHz·mm) of frequency f and (wall) thickness d for various modes: symmetrical modes S0 and S1, asymmetrical modes A0 and A1, and sheer mode SH0. Other modes exist but are less relevant to the present invention and are therefore omitted from FIG. 4.

It can be seen that the graph of the S0 mode can be said to comprise three sections: a first section approximately between f×d=0 and f×d=2 (in the present example) where the velocity c is relatively high, a second section approximately between f×d=2 and f×d=3 (in the present example) where the velocity decreases relatively rapidly, and a third section approximately above f×d=3 (in the present example). The points separating these sections are indicated in FIG. 4 as bending points BP1 and BP2: below the first bending point BP1 the velocity is relatively high (approximately 5800 m/s in the example shown); between the bending points BP1 and BP2 the velocity decreases relatively rapidly, and above the second bending point BP2 the velocity is relatively low (approximately 3000 m/s in the example shown). As mentioned above, the Prior Art method of JP 2007-3537 uses a frequency at the second bending point or point of inflection BP2. The present inventors have found that this choice of frequency is not suitable for objects containing liquids, such as pipes or vessels containing oil or water, as the attenuation at this frequency is too high for the method to be useful. This will be illustrated with reference to FIG. 5.

FIG. 5 schematically shows the S0 mode graph, together with a graph of the attenuation α (in dB/m). As can be seen, the attenuation α is, at the second bending point BP2, approximately equal to 75 dB/m. In practice this means that the power of the ultrasonic waves reaching the transducer units 5 will be negligible, making their detection extremely difficult, if not impossible.

In contrast, the present invention suggests to use a frequency (or frequency range) at or below the first bending point BP1. It is clear from FIG. 5 that the attenuation α at such a frequency is less than 18 dB/m, thus providing an improvement of 57 dB/m. Accordingly, the method and device according to the present invention can also be used for liquid-filled objects.

It is noted that the terms "bending point" and "point of inflection" are used interchangeably in this document. In a strict mathematical sense, the bending points BP1 and BP2 of the S0 curve in FIG. 5 are not points of inflection: the S0 curve shown has a single point of inflection located halfway between the bending points BP1 and BP2. This (mathematical) point of inflection is the point where the slope of the curve changes from increasing into decreasing. However, the bending points BP1 and BP2 may also be referred to as "points of inflection", as at these bending points the curve bends or inflects. In fact, the S0 curve exhibits a maximum curvature at these bending points.

As can be seen from FIG. 5, the first bending point BP1 is located at f×d=2 (MHz·mm). As the graph of FIG. 5 is based upon a wall thickness d of 6 mm, the corresponding frequency is 0.33 MHz=330 kHz. It can thus be said that (given a wall thickness of 6 mm) the present invention uses frequencies of at most approximately 330 kHz, for example 330 kHz, 300 kHz or 250 kHz, although lower frequencies may also be used. By using such frequencies, the attenuation caused by a fluid-filled object is significantly reduced.

To further improve the modelling of an object, a waveform correction may be used to correct dispersive waves. This is schematically illustrated in FIGS. 6A and 6B, where FIG. 6A shows an original pulse 81 (thick line) and its distorted counterpart 82 (thin line), while FIG. 6B shows a reconstructed pulse 83.

In FIG. 6A, a pulse 82 is shown to be distorted due to dispersion: the original phase relationship of the pulse is lost and the pulse is spread out in time, as compared to the original pulse 81. This makes the determination of the arrival time of the pulse, and hence its travel time, less accurate. This is particularly relevant when multiple paths are used, as illustrated in FIG. 3.

The loss of accuracy due to dispersion may be avoided by optionally applying a waveform correction. In International Patent Application WO 2008/103036 (TNO) this waveform correction (phase correction) is achieved by multiplying the frequency spectrum of the distorted pulse with a frequency domain correction factor. After correction, the phase and hence shape of the pulse is restored, as illustrated in FIG. 6B. This restored pulsed wave 83 allows an accurate detection of its travel time.

A device for modelling a surface of an object is illustrated in FIG. 7. The device 1 comprises a processing unit (PU) 10, a memory unit (11), a transmission unit (TU) 12 and a display unit (DU) 13. The processing unit 10 preferably comprises a microprocessor capable of executing instructions of a software programme embodying the method of the present invention. The memory unit 11 may store this software programme, as well as parameters of the model, including the set of surface point values. The display unit 13 preferably comprises a display screen capable of displaying the model, in particular a reconstruction of the type illustrated in FIG. 2. The transmission unit 12 is capable of producing, under control of the processing unit 10, pulse transmission signals which are fed to the first transducer(s) 4. In addition, the transmission unit 12 is capable of receiving pulse detection signals produced by the second transducer(s) 5 and feeding suitable pulse detection information to the processing unit 10.

The transmission unit 12 may be arranged for wireless communication with the transducers 4 and 5, for example using radio frequency (RF) communication or infrared communication. The processing unit 10 may additionally be arranged for applying a waveform correction (de-smearing). Suitable programme steps for waveform correction may be stored in the memory unit 11.

In accordance with the present invention, the transmission unit 12 and the transducer units 4 and 5 are arranged for operating at a frequency at or below the first bending point (BP1 in FIGS. 4 & 5) of the S0 graph.

It will be understood that the invention is not limited to pipes or tubes but may also be applied on the surfaces or walls of other objects, for example (parts of) ship hulls, airplane fuselages, car bodies, tank armour, or other surfaces or wall structures, for example storage tanks, rods, steel bridges, and metal structures in buildings.

The present invention is based upon the insight that the frequencies at or below the first bending point ("first point of inflection") of the S0 mode curve involve significantly less attenuation than those at the second bending point ("second point of inflection"), and are therefore much more suitable for measurements. The present invention is particularly suitable for, but certainly not limited to, multipath applications. In other words, the present invention may also be used in single path applications.

It is noted that any terms used in this document should not be construed so as to limit the scope of the present invention. In particular, the words "comprise(s)" and "comprising" are not meant to exclude any elements not specifically stated. Single elements may be substituted with multiple elements or with their equivalents.

It will be understood by those skilled in the art that the present invention is not limited to the embodiments illustrated above and that many modifications and additions may be made without departing from the scope of the invention as defined in the appending claims.

The invention claimed is:

1. A method of modeling a surface of an object by using ultrasonic waves transmitted along the surface, the method comprising the steps of:
  transmitting, with a first transducer, the ultrasonic waves along paths along the surface,
  receiving, with at least one second transducer, the ultrasonic waves along the paths along the surface, and
  determining, with a processing unit, travel times of the ultrasonic waves along the paths,
  wherein at least some of the ultrasonic waves exhibit a symmetrical zero-order (S0) mode and have a frequency-dependent velocity having a first bending point (BP1) and a second bending point (BP2), which velocity (c) is higher for frequencies up to a first bending point (BP1) than for frequencies beyond the second bending point (BP2), wherein the velocity (c) decreases more rapidly for frequencies between the first bending point (BP1) and the second bending point (BP2), than for frequencies up to the first bending point (BP1) and beyond the second bending point (BP2)
  wherein the object has a circumference, wherein the ultrasonic waves have a frequency range which lies at or below the first bending point (BP1), and wherein some paths of the ultrasonic waves between the first transducer and the least one second transducer extend at least once around the circumference.

2. The method according to claim 1, wherein the frequency range is chosen such that the product of wall thickness and frequency in said frequency range is equal to or less than 2.0 MHz·mm.

3. The method according to claim 1, wherein the frequency range has a bandwidth of less than 150 kHz, preferably less than 120 kHz.

4. The method according to claim 1, wherein the ultrasonic waves are pulsed waves.

5. The method according to claim 1, wherein the ultrasonic waves are guided waves or Rayleigh waves.

6. The method according to claim 1, wherein the object is a pipe for transporting liquids, preferably oil or water.

7. The method according to claim 1, wherein the object is a vessel for storing liquids, preferably oil or water.

8. A non-transitory computer readable medium containing computer instructions stored therein causing a computer process to carry out the method according to claim 1.

9. A device for modeling a surface of an object by using ultrasonic waves transmitted along the surface, the device comprising:
  a first transducer and at least one second transducer, the first transducer and each second transducer defining paths along the surface,
  a transmission unit for transmitting the ultrasonic waves along the paths from the first transducer to each second transducer, and
  a processing unit arranged for determining travel times of the ultrasonic waves along the paths,
  wherein at least some of the ultrasonic waves exhibit a symmetrical zero-order (S0) mode and have a frequency-dependent velocity having a first bending point (BP1) and a second bending point (BP2), which velocity (c) is higher for frequencies up to a first bending point (BP1), than for frequencies beyond the second bending point (BP2), wherein the velocity (c) is decreasing more rapidly for frequencies between the first bending point (BP1) and the second bending point (BP2) than up to the first bending point (BP1) and beyond the second bending point (BP2)
  wherein the object has a circumference, wherein the ultrasonic waves have a frequency range which lies at or below the first bending point (BPI), and wherein some paths of the ultrasonic waves between the first transducer and the least one second transducer extend at least once around the circumference.

10. The device according to claim 9, wherein the frequency range is chosen such that the product of wall thickness and frequency in said frequency range is equal to or less than 2.0 MHz·mm.

11. The device according to claim 9, which preferably has a bandwidth of less than 150 kHz, more preferably less than 120 kHz.

12. The device according to claim 9, wherein the ultrasonic waves are pulsed waves, preferably guided waves or Rayleigh waves.

13. The device according to claim 9, further comprising a display unit for displaying a model of the surface.

14. The device according to claim 9, further comprising a memory unit for storing a model of the surface.

15. A system for monitoring objects, the system comprising a device according to claim 9, wherein the object preferably is a pipeline, more preferably a pipeline for transporting liquids.

* * * * *